(12) United States Patent
Somekh et al.

(10) Patent No.: US 9,470,629 B2
(45) Date of Patent: Oct. 18, 2016

(54) SURFACE PLASMON MICROSCOPY

(71) Applicant: The University of Nottingham, Nottingham (GB)

(72) Inventors: Michael Geoffrey Somekh, Nottingham (GB); Chung Wah See, Nottingham (GB)

(73) Assignee: The University of Nottingham, Nottingham (GB)

(*) Notice: Subject to any disclaimer, the term of this patent is extended or adjusted under 35 U.S.C. 154(b) by 30 days.

(21) Appl. No.: 14/429,243

(22) PCT Filed: Sep. 18, 2013

(86) PCT No.: PCT/GB2013/052436
§ 371 (c)(1),
(2) Date: Mar. 18, 2015

(87) PCT Pub. No.: WO2014/045027
PCT Pub. Date: Mar. 27, 2014

(65) Prior Publication Data
US 2015/0247796 A1 Sep. 3, 2015

(30) Foreign Application Priority Data

Sep. 18, 2012 (GB) .................................. 1216645.0

(51) Int. Cl.
| | |
|---|---|
| *G01N 21/55* | (2014.01) |
| *G01N 21/552* | (2014.01) |
| *G02B 21/00* | (2006.01) |
| *G01N 21/21* | (2006.01) |

(52) U.S. Cl.
CPC .............. *G01N 21/55* (2013.01); *G01N 21/21* (2013.01); *G01N 21/553* (2013.01); *G02B 21/0024* (2013.01)

(58) Field of Classification Search
CPC .. G01N 21/55; G01N 21/21; G02B 21/0024; G01B 9/02057
See application file for complete search history.

(56) References Cited

U.S. PATENT DOCUMENTS

| 5,442,448 A * | 8/1995 | Knoll ...................... G02B 6/122 |
| | | 356/445 |
| 2006/0116859 A1* | 6/2006 | Legault ............. G06F 17/30554 |
| | | 703/22 |
| 2007/0258096 A1 | 11/2007 | Cui et al. |

FOREIGN PATENT DOCUMENTS

| FR | 2942049 | 8/2010 |
| WO | WO-01/92858 | 12/2001 |

OTHER PUBLICATIONS

International Search Report and Written Opinion for PCT/GB2013/052436 mailed Jan. 21, 2014.

(Continued)

*Primary Examiner* — Jonathan Hansen
(74) *Attorney, Agent, or Firm* — Paul M. H. Pua; Foley & Lardner LLP (57) ABSTRACT

Surface plasmon microscopy methods are described which comprise irradiating a sample with a beam of electromagnetic radiation, wherein at least some of the radiation is incident on the sample at an angle or angles which results in the excitation of surface plasmons in the sample, and wherein the beam of radiation comprises a longitudinal axis passing through a focus of the beam. Both radiation reradiated from the sample by one or more surface plasmons and radiation reflected from a location on the sample which does not lie on the longitudinal axis passing through the focusare received at a detector. The received reradiated radiation is then interfered with the received reflected radiation to provide information about the sample. Apparatus for performing the methods is also described.

18 Claims, 8 Drawing Sheets

(56) References Cited

OTHER PUBLICATIONS

Zhang, Bei et al., "Confocal surface plasmon microscopy with pupil function engineering," Optics Express, (Mar. 26, 2012), vol. 20, No. 7, pp. 7388-7397.

Zhang, Bei et al., "Quantitative plasmonic measurements using embedded phase stepping confocal interferometry," Optics Express, (May 6, 2013), vol. 21, No. 9, pp. 11523-11535.

Zhang, Bei et al., "Surface plasmon microscopic sensing with beam profile modulation," Optics Express, (Dec. 17, 2012), vol. 20, No. 27, pp. 28039-28048.

* cited by examiner

SURFACE PLASMON MICROSCOPY

RELATED APPLICATIONS

This application is the U.S. National Stage of International Application Number PCT/GB2013/052436, filed Sep. 18, 2013, which claims the benefit of and priority to GB Application Number 1216645.0, filed Sep. 18, 2012. The entire contents of the foregoing are hereby incorporated by reference.

The present invention relates to methods and apparatus for surface plasmon microscopy, and particularly, but not exclusively, to methods and apparatus using linearly polarised radiation to excite surface plasmons.

Surface plasmons occur when electromagnetic radiation incident on a surface, in particular a metal-dielectric boundary, couples to that surface and is guided along it as a wave. The angle of illumination at which surface plasmons are excited is extremely specific to the properties of the surface being irradiated. As a surface plasmon travels along the surface, it continually reradiates electromagnetic energy at the same angle as the radiation which originally excited it until it disperses some tens of microns later.

From a microscopy point of view, the interest in surface plasmons lies in the fact that the propagation properties of surface plasmons are very strongly affected by the properties of the surface along which they travel. Even an atomic layer of material deposited on the surface will perturb the angle at which surface plasmons are excited to a measurable level. This has led to the widespread use of surface plasmon systems as chemical and biological sensors.

Surface plasmon sensors are already finding a great deal of application in the field of diagnosis of infectious and degenerative disease states. In many cases it is necessary to use multiple biomarkers to obtain a reliable diagnosis. Furthermore, with the growing possibilities in personalized medicine clinicians are demanding the capacity to stratify disease risk factors as well as make distinctions between different subtypes.

Cytokines are signalling proteins that are highly responsive to disease state, often changing concentrations by several orders of magnitude in response to particular disorders. It certainly seems that the major key to precise and specific diagnosis in the years to come lies in monitoring levels and patterns of cytokines, particularly the interleukins. Unfortunately the concentration of cytokines is tiny compared to other common plasma based proteins, typically of the order of pg/mL compared to e.g. albumin or fibrinogen which may be present in concentrations $10^8$ to $10^9$ times larger. This means that there is a need to perform measurements with small concentrations of chemicals; clearly also for routine healthcare the size of the sample is limited, this means that the total number of molecules is also limited which, in turn, places a requirement on the technology to perform measurements on small numbers of molecules. The demands on sensor technology are not just limited to detection—we may also want to measure binding affinity and small changes in concentration. These features together impose a need to measure low numbers of molecules with simple inexpensive and reliable technology. We believe surface plasmon techniques may allow us to approach these levels of sensitivity without the experimental variability of tip enhanced methods.

A problem with existing surface plasmon microscopy systems has been their limited lateral resolution (i.e. along the sample surface). The usual explanation for this poor resolution is that surface plasmons, once excited, spread over a large area of the sample surface, since their decay length is of the order of tens of microns as mentioned earlier. It can therefore be difficult to improve the lateral resolution to much better than this value.

In International patent publication WO01/92858 we proposed a high resolution surface plasmon microscopy method in which surface plasmons were confined to an area of the sample surface, thus improving the lateral resolution. Subsequently we showed that this method could be implemented within a confocal microscope configuration (Confocal surface plasmon microscopy with pupil function engineering; Bei Zhang, Suejit Pechprasarn, Jing Zhang, and Michael G. Somekh; Optics Express, Vol. 20, Issue 7, pp. 7388-7397 (2012)). We discussed further improvements to this method in our subsequent papers: Surface plasmon microscopic sensing with beam profile modulation; Bei Zhang, Suejit Pechprasarn, and Michael G. Somekh; Optics Express, Vol. 20, Issue 27, pp. 28039-28048 (2012) and Quantitative plasmonic measurements using embedded phase stepping confocal interferometry; Bei Zhang, Suejit Pechprasarn, and Michael G. Somekh; Optics Express, Vol. 21, Issue 9, pp. 11523-11535 (2013). Further improvements to this method are described herein.

According to a first aspect of the invention there is provided a surface plasmon microscopy method comprising:
    irradiating a sample with a beam of electromagnetic radiation, wherein at least some of the radiation is incident on the sample at an angle or angles which results in the excitation of surface plasmons in the sample, and wherein the beam of radiation comprises a longitudinal axis passing through a focus of the beam;
    receiving at a detector radiation reradiated from the sample by one or more surface plasmons;
    receiving at a detector radiation reflected from a location on the sample which does not lie on the longitudinal axis passing through the focus; and
    interfering the received reradiated radiation with the received reflected radiation.

In our previously proposed method, radiation reradiated from the sample by one or more surface plasmons was interfered with radiation directly reflected from the sample along the longitudinal axis of the beam. However, we have found that using off-axis reflected radiation as set out above (and described in more detail in the specific description below) can result in an improved image, as the resulting signal is less affected by background noise produced by, for instance, microphonics.

The received reference reflected radiation may be reflected at an angle θ which is substantially the same as the angle or angles at which surface plasmons are generated. Typically this means that the reflected radiation is reflected from a similar radial position on the sample surface to the received radiation reradiated by the one or more surface plasmons. The path traveled by both beams is thus similar, resulting in a method that is substantially common path.

Where the angle at which surface plasmons are excited is $\theta_p$, the angle θ of the reflected reference radiation may comprise $\theta_p \pm 10°$, or $\pm 5°$, or $\pm 1°$, or $\pm 0.5°$, or $\pm 0.1°$. As discussed above, the closer θ is to $\theta_p$, the closer the method is to common path.

The beam of electromagnetic radiation may be polarized. In prior art systems the use of radial polarization incident in the back focal plane has often been advocated, which means the light incident on the sample is p-polarized for all azimuthal angles, so that more energy is coupled in surface plasmons and the focus is tight and circularly symmetrical.

In the present system however, the beam of electromagnetic radiation may be linearly polarized.

When linear polarized light is incident on the back focal plane of a microscope objective the resulting radiation on the sample comprises two components, p-polarization and s-polarization. The received reradiated radiation may comprise p-polarized radiation, and the received reflected radiation may comprise s-polarized radiation. As mentioned above, these two components of detected radiation are forced to interfere by an appropriate mechanism. The appropriate mechanism may comprise deflecting the path of the reflected or incident radiation (possibly by deflecting a part of the incident radiation that will subsequently be reflected) through a deflection angle d. The deflection may be achieved using any suitable path deflection mechanism, such as refraction, reflection or a phase gradient. The deflection angle d is dependent upon the configuration of the optical system (for example, sample defocus and system magnification) but will in general be a small fraction of a degree (e.g. ½, ⅕, ¹⁄₁₀, ¹⁄₁₀₀ of a degree). The deflection angle is preferably selected so that light reflected at a selected angle from the sample surface, which would not otherwise be detected, is caused to reach the detector. The selected angle is preferably the same, or substantially the same, as the angle of excitation of surface plasmons.

It will be appreciated that although the above concepts have been described with reference to linear polarisation, they are also applicable to other polarization states where light incident on the sample can be split into two parts that give rise to s- and p-polarizations incident at the sample.

The method may further comprise masking the electromagnetic beam such that radiation on the longitudinal axis of the system is not detected. The masking may comprise masking an area of a detector; and/or masking an area of the beam; and/or programming a detector to disregard radiation detected in a pre-programmed area.

The method may be confocal. Alternatively, the method may be interferometric.

According to a second aspect of the invention, there is provided a surface plasmon microscopy system adapted to perform the method described above with reference to the first aspect of the invention.

The system may include a path altering element operable to deflect the path of the reflected radiation through a deflection angle d. The path altering element may be operable to deflect radiation incident on the sample (i.e., may be located in the path of the incident beam), and/or may be operable to deflect radiation reflected from the sample (i.e. may be located in the path of the return beam). The path altering element may be located in a back focal plane of the optical system.

The path altering element may comprise a spatial light modifier (SLM) having a phase gradient in a region through which the path of the reflected radiation is intended to pass. The phase gradient may be substantially linear, or may comprise a curve. If curved, the curve of the phase gradient may comprise a cubic component.

The system may comprise a masking element operable to mask the electromagnetic beam such that radiation on the longitudinal axis of the system is not detected. The masking element may comprise the (or an additional) spatial light modifier.

According to a third aspect of the invention, there is provided a computer program encoded on a computer readable medium, the computer program operable, when run, to cause a surface plasmon microscopy system to carry out the method described above with reference to the first aspect of the invention.

An embodiment of the invention will now be described, by way of example only, with reference to the accompanying drawings, in which.

Figure 1:
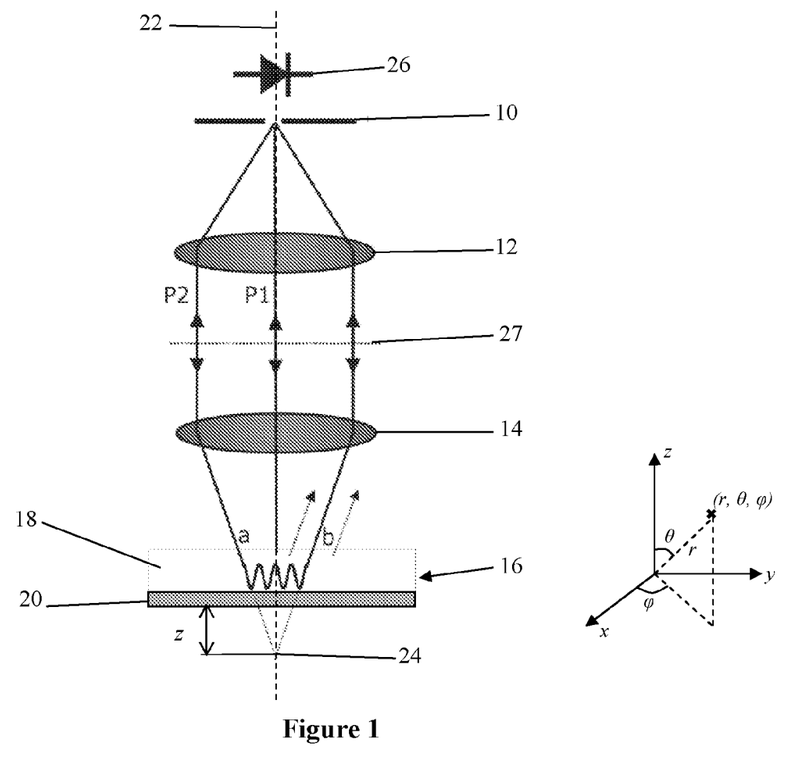
FIG. 1 is a schematic diagram illustrating the principle of operation of a confocal surface plasmon microscopy system.

FIG. 1 schematically demonstrates the principle behind a confocal surface plasmon microscope. For clarity this does not show the illumination source. This is, however, shown in FIGS. 8 and 10. The microscope includes a pinhole 10 through which electromagnetic radiation 11 is detected. An imaging system comprising first 14 and second 12 lenses directs radiation from the sample 16 onto the pinhole. The first lens 14 is, in this example, an oil immersion objective lens to better couple the incident radiation to the sample and excite surface plasmons. The sample itself comprises a glass slide 18 backed with a metal 20 such as gold, on which a test substance may have been deposited.

Incident electromagnetic radiation in the form of a beam having a longitudinal axis 22 and a focus 24 lying on the longitudinal axis is directed onto the sample by illumination optics (not shown in FIG. 1). As used herein, 'longitudinal axis' refers to an axis of the beam of incident radiation coinciding with the overall propagation direction of the beam, and is not intended to imply that the radiation is incident on the sample surface at any particular angle (i.e. normal incidence is not necessary).

The sample 16 is positioned off the focal plane of the apparatus (that is, above, the plane containing the focus) and perpendicular to the longitudinal axis of the beam. This results in a generally circular area of the sample being irradiated. Electromagnetic radiation incident on the sample is reflected back from the sample towards the lens array, where it is focused and directed back towards the pinhole 10. The pinhole functions to block out all light which does not appear to come from the focus. In this case the radiation that passes through the pinhole to be detected may be considered to be in two parts which appear to emerge from the focus 24.

In the normal course of events (without excitation of surface plasmons), this means that only light directly reflected from the sample along the longitudinal axis of the beam (i.e., along path P1) can reach a detector 26 located on the far side of the pinhole. However, in the event that at least some of the radiation incident on the sample surface is at an angle or angles that cause surface plasmons to be excited on the sample surface, light from a second path (P2) is able to reach the detector. In particular, when light is incident on the sample at the correct angle for excitation of surface plasmons, this generates surface plasmons at position 'a'. The surface plasmons travel along the sample surface, reradiating light at all positions. However, in the confocal system shown only the light appearing to come from the focus (i.e. reradiating at 'b') is able to pass through the pinhole. Similarly, surface plasmons excited at 'b' and reradiating at 'a' also make a contribution.

Thus there are only two principal possible paths for radiation to travel through the confocal apparatus shown in FIG. 1: the path normal to the sample (P1), and a path having an incident polar angle (θ) operable to excite surface plasmons in the sample (P2). (It will be appreciated that in reality there are a plurality of paths P2, originating from an annulus of the sample surface which is centered on the focus—these paths are collectively referred to herein as 'path P2'). Radiation from paths P1 and P2 can be interfered together to give information about the sample. In particular, as the defocus distance z is varied the output V varies. The relative phase φ(z) between the P1 and P2 contributions changes, leading to an oscillating signal whose period depends on the angle of incidence at which surface plasmons are excited.

The system of FIG. 1 has considerably improved resolution over prior systems, due to the fact that the surface plasmons are confined to a substantially circular area of the sample surface by the defocused arrangement. However, this system has a problem in that it is sensitive to shot noise, and in particular microphonics. For instance, imagine the sample position is subject to noise in the axial direction, $\Delta z$. Thus although the paths P1 and P2 appear constant, a phase noise given by $2kn\Delta z(1-\cos\theta_p)$ is introduced, where $\theta_p$ denotes the angle of incidence of the radiation which excited the plasmon (following path P2), and $1=\cos\theta$ where $\theta=0$ is the angle of incidence of the radiation following path P1.

Figure 2:
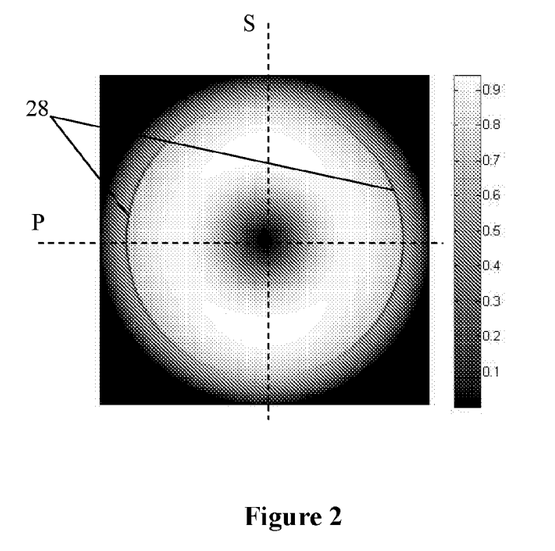
FIG. 2 shows an electromagnetic amplitude distribution as measured at the back focal plane for the system of FIG. 1.
Figure 3:
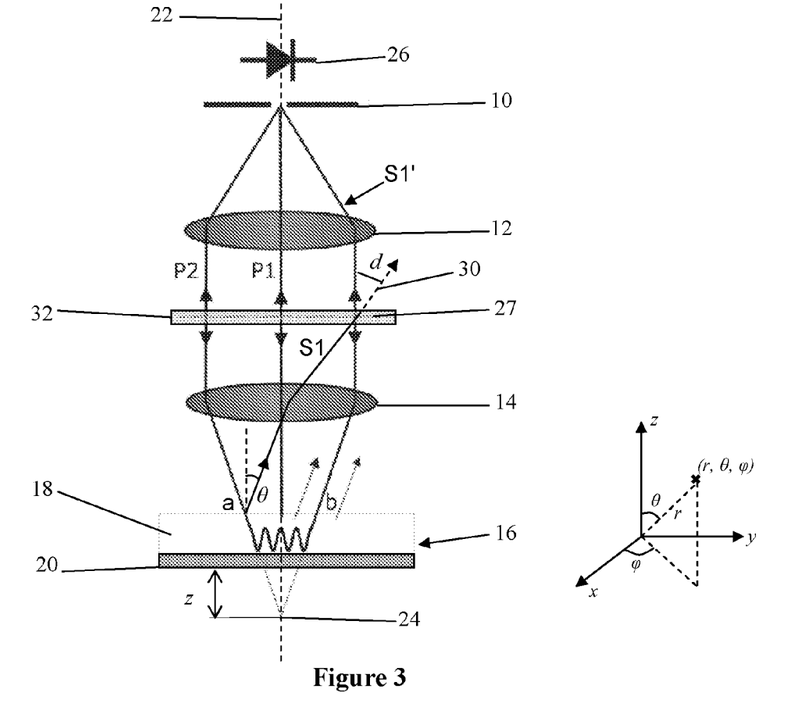
FIG. 3 is a schematic diagram similar to FIG. 1 illustrating a principle of the invention.
Figure 4:
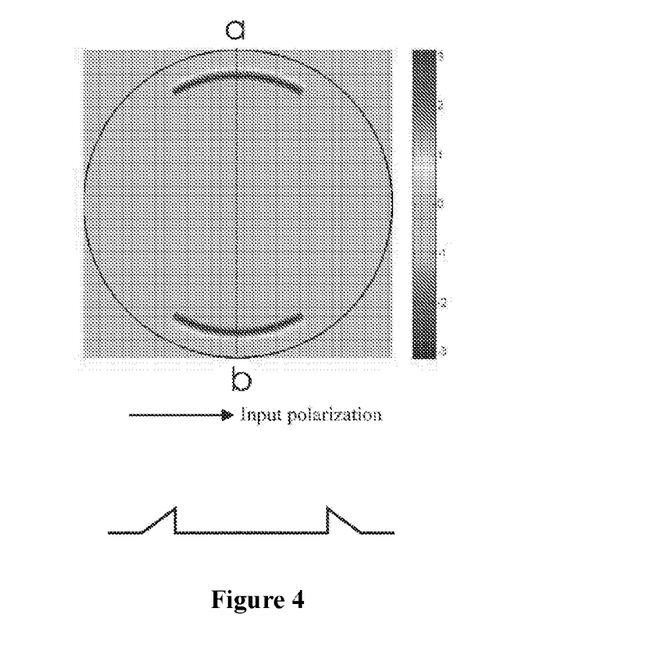
FIG. 4 shows the phase profile of the back focal plane insert of FIG. 3.

Referring now to FIGS. 2 to 4, a method of reducing the effect of this phase noise will be discussed.

FIG. 2 shows a back focal plane amplitude distribution of the type that might be seen at the back focal plane 27 of the lens arrangement of FIG. 1. Dips in amplitude (darker areas) that are due to surface plasmon excitation can be seen at 28. The large black area in the middle of FIG. 2 is present because the angles close to normal incidence have been blocked out, as will be discussed later. The input polarization of the electromagnetic radiation that produced FIG. 2 was linear, so strong dips are seen along the direction of incident polarization (marked by line P) where there is more p-polarization. Surface plasmons are not excited by s-polarized radiation, and so substantially no dips are seen in the direction perpendicular to this one (marked by line S). (N.B. p-polarization occurs when the plane of polarization of a wave is parallel to the plane of incidence of the wave. s-polarization occurs when the plane of polarization is perpendicular to the plane of incidence.)

As discussed above, P1 and P2 are the only available paths through the confocal pinhole of FIG. 1. However, path P2 is not available to s-polarized radiation, because it is not capable of exciting surface plasmons. Instead, s-polarized radiation is specularly reflected from the sample and blocked out by the pinhole. However, if the s-polarized radiation were able to interfere with the p-polarized radiation, the noise due to microphonics would be reduced to $2kn\Delta z(\cos\theta_s-\cos\theta_p)$ where the subscript s refers the s-polarized radiation and the subscript p refers the p-polarized radiation. It can be seen that the more similar the angles θ from which the s and p-polarized contributions originate, then the smaller the term in brackets. If the s and p-polarized contributions originate from substantially the same angles, then the term in brackets can be made vanishing small.

FIG. 3 schematically shows an implementation of the principle discussed above. Like FIG. 1 the illumination source is omitted for clarity. Like reference numerals in FIG. 3 indicate like components to those described with reference to FIG. 1, and so only differences are discussed below.

In addition to paths P1 and P2, FIG. 3 shows a third path S1. Radiation which is incident on the sample at an angle θ is specularly reflected at the same angle θ along path S1. Because the reflected radiation following path S1 does not appear to originate from the focus 24, it is not focused towards the pinhole 10 by lens 14. In the system of FIG. 1, such radiation would be directed away from the detector 26, for example along a path 30, indicated by a dotted line in FIG. 3, and blocked out by the pinhole 10.

However, the arrangement of FIG. 3 additionally comprises a path deflection element in the form of an insert 32 located in the back focal plane of lenses 12 and 14. The back focal plane insert 32 is operable to modify, and in particular deflect, radiation following path S1 through a preselected deflection angle d until it appears to come from the focus 24. This radiation then continues along a modified path S1' (substantially similar to P2) as an 'artificial plasmon' and is focused onto the detector by lens 12. The result is a system with two different components of radiation, one s-polarized (S1/S1') and one p-polarized (P2), reaching the detector from substantially the same radial position on the sample. The noise component inherent in interfering these two components is significantly smaller than the noise component present when interfering radiation from paths P1 and P2. If required, radiation following path P1 can be reduced or even eliminated, for example by providing a mask in the back focal plane or over the central region of the detector as indicated in FIG. 2.

In addition to compensating for mechanical vibrations it is also necessary to cancel out temperature fluctuations. In addition to the usual approach of stabilizing the temperature, it is common practice to have a reference channel in which the biochemical reaction does not occur but which suffers essentially similar temperature fluctuations to the sample channel. The results from the reference and sample channels are subtracted to give a measurement that is largely independent of temperature effects. Since adjacent measurement spots are much closer in microscopic based surface plasmon systems compared to conventional plasmon systems the temperature between sample and reference channels will be even better correlated thus allowing for more complete temperature compensation with the methods described herein.

The back focal plane insert can be of any suitable configuration operable to bend light reflected at a selected angle or angles (or from a selected radial position or positions) such that it will be focused by the optics of the system onto the detector. One example of such an insert is a prism. Another example is a spatial light modulator in which a radially varying phase gradient is imposed in the back focal plane on the radiation with predominantly s-polarization at the incident angle associated with the surface plasmon this phase gradient will deflect radiation in a similar manner to the prism. FIG. 4 shows a profile of a suitable spatial light modifier along the line ab, which coincides to the plane of s-polarization (line S in FIG. 2).

Figure 5:
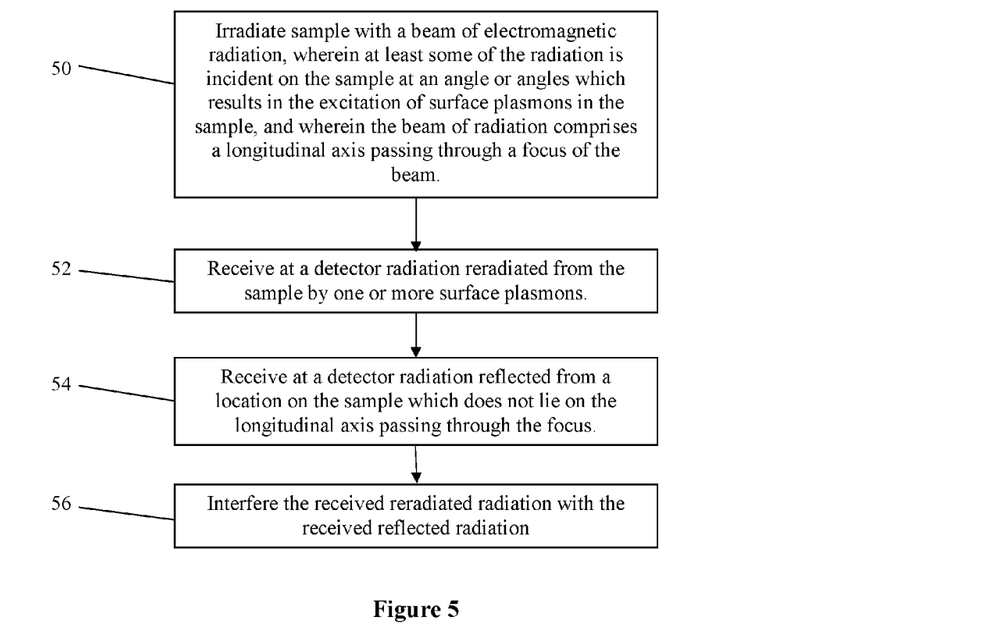
FIG. 5 is a flow chart schematically depicting a surface plasmon microscopy method.

FIG. 5 is a flow chart schematically setting out a method utilising the principles explained above. In block 50 a sample (which might for instance be a glass coverslip backed with a metal foil on which a biological substance for test has been deposited) is irradiated with a beam of electromagnetic radiation, for example laser light. The beam of radiation comprises a longitudinal axis passing through a focus of the beam, and at least some of the radiation incident on the sample is at an angle or angles which results in the excitation of surface plasmons in the sample. As discussed above, the electromagnetic radiation might be in the form of a defocused beam, which has the effect of irradiating the sample over a wide range of angles substantially simultaneously. An annular mask might be provided for the beam to block out radiation which is close to normal incidence, and/or which is not expected to generate surface plasmons.

In block 52, radiation reradiated from the sample by one or more surface plasmons is received at a detector. This radiation comprises information about the sample surface, as the angle at which a surface plasmon reradiates is closely affected by the material of the sample surface.

In block 54, radiation reflected from a location on the sample which does not lie on the longitudinal axis passing through the focus is received at a detector (which may be the same detector as that mentioned in block 52). That is, reflected radiation which is NOT normal to the focal plane is received at a detector. The radiation is ideally reflected at an angle of incidence which is similar to that necessary to excite surface plasmons, but has a polarization such that this is suppressed.

As discussed above, one method of achieving the detection of such reflected radiation is to alter the path of radiation reflected from the sample at a selected angle or range of angles, for example by inserting a path-altering element into the back focal plane of the lens system which is being used. Another method (discussed in more detail below) is to alter the path of a portion of the incident beam in a similar manner (i.e. by use of a path deflecting insert in a back focal plane), such that the deflected radiation is reflected from the sample at the selected angle or range of angles and focussed by the system optics onto the detector. In either case, the closer the selected angle is to the angle of excitation of surface plasmons, the better the resulting image.

Blocks 52 and 54 can be performed in any order, and in some examples, such as the one discussed above, are performed substantially simultaneously.

Finally, in block 56, the received reradiated radiation (block 52) and the received reflected radiation (block 54) are interfered. That is, the reradiated components (block 52) which were predominantly involved in the plasmonic excitation are interfered with those that were directly reflected from the sample (block 54). The phase difference between the two paths can be analysed to provide information about the surface of the sample under test. For example, as the defocus distance z is varied, the phase difference between the paths alters, changing the contrast of the image.

Figure 6:
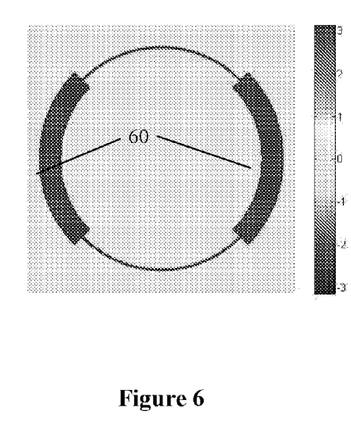
FIG. 6 shows example phase shifting.

The above method can be used to provide a substantially common path interferometer which is very sensitive to minute changes in surface plasmon propagation and which has a confinement far superior to a conventional prism or grating based surface plasmon detection systems. In order to recover the phase difference between the reradiated and reflected radiation phase stepping can be used, an example of which is shown in FIG. 6. The solid arcs 60 act on the 'true' plasmon (originating via path P2). This can be phase shifted to get the best contrast or signal change with the artificial plasmon (originating via path S1/S1') for a given refractive index change. Alternatively we can perform phase stepping and recover the relative phase of the true and artificial plasmons.

Figure 7:
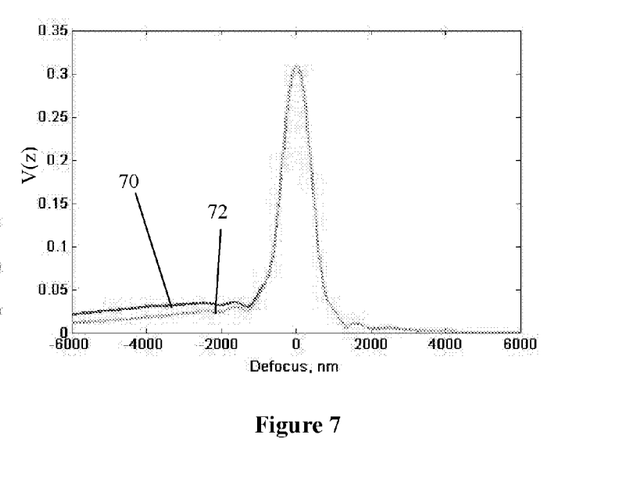
FIG. 7 shows the output signal V(z), where V is the output and the x-axis is the defocus for refractive indices of 1 and 1.02 (i.e. a refractive index change of 2e−2)

FIG. 7 shows calculated system output magnitudes (V(z)) obtained with pupil function of FIG. 2. Line 70 has a refractive index of 1 and, and line 72 has a refractive index of 1.02. We can see that as with a normal V(z) there is little difference at positive defocus. However, at negative defocus the signals differ due to excitation of real and artificial plasmons. Note that there is no ripple in the curves since the phase of the two components vary at almost the same rate.

Preliminary calculations show that this approach is capable of measuring of the order of 10-30 molecules without modification of the metal layer. Single molecule detection should be possible with modified nanostructured surfaces and with appropriate positioning of the analyte at the focus of the surface plasmons.

Figure 8:
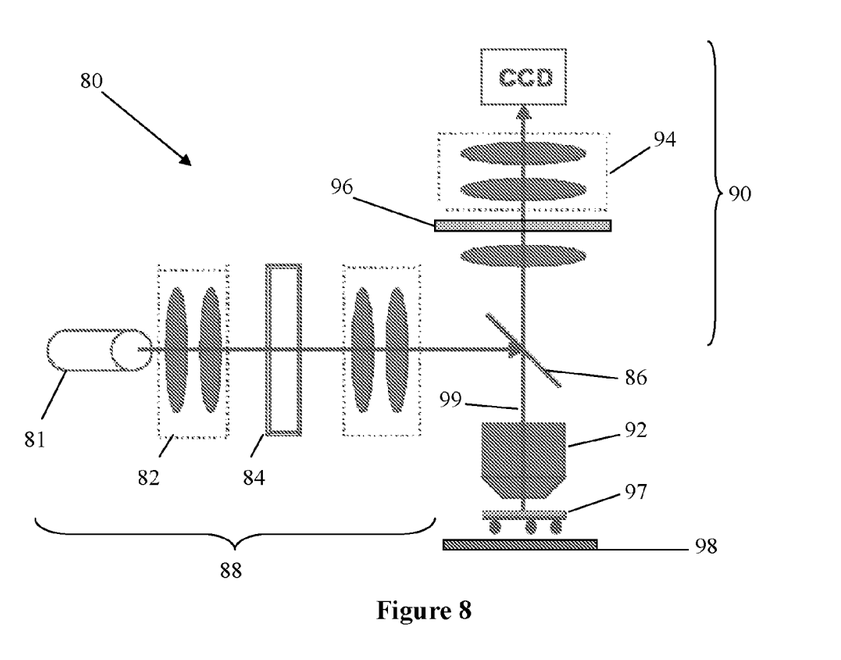
FIG. 8 is a simplified schematic diagram of a confocal microscopy system having a path deflection element in the beam return path.

FIG. 8 shows a simplified schematic of a confocal surface plasmon microscopy system 80. A radiation source 81, in particular a laser, and in this case a 632.8 nm He—Ne laser (10 mW), was used as the source of the electromagnetic beam. In the example set up shown, beam expanders 82 were used to increase the beam diameter of the beam incident onto a spatial light modulator 84 (SLM) which was conjugate with the back focal plane (BFP) of the immersion objective. The SLM was used to control the effective illumination pattern in the BFP.

A beam splitter 86, in this case a pellicle beam splitter, was used to separate the illumination and imaging paths (numbered 88 and 90 respectively in FIG. 8). The microscope objective 92 used in this example was a 1.25 NA (numerical aperture) oil immersion objective, which had sufficient aperture to excite surface plasmons in air. For operation in aqueous media NAs in the range 1.45 to 1.65 are necessary. The light distribution reflected from the sample was imaged onto a detector, in this case a CCD camera which served as a variable pinhole. The light from the sample was magnified by approximately 1000 times from the sample to the CCD plane by magnification optics 94 so that a point spread function occupied >100 pixels. This allowed the pinhole radius to be readily controlled by selecting different regions of camera. Moreover, spreading the returning beam reduced the problem of saturating individual pixels.

A path-altering element 96, in this example a second SLM, was inserted into the back focal plane of the detection optics in order to alter the path of s-polarised light reflected from the sample at a desired angle or angles, in line with the method discussed above.

Samples 97 were mounted in a 3-dimensional (3D) scanning system 98, which consisted of a 3 axis mechanical stage drive, piezoelectric actuators (P621.1CD, Physik Instrumente) stage and (P-541.2CD, Physik Instrumente) giving 1 and 2 axes of movement respectively. Samples were prepared by coating gold with or without BSA (bovine serum albumin) on cover glasses; 2 nm chromium was coated between gold and cover glasses to improve the adhesion.

In use, the sample 97 was illuminated with radiation from the laser 82, via the illumination path 88 and the objective lens 92. Radiation both reflected and reradiated from the sample was directed towards the CCD detector via the objective lens and the imaging path 90. As mentioned above, the CCD was programmed to function as a pinhole. Therefore, only light appearing to come from the focus of the optical system was detected by the appropriate region of the CCD detector. Such light includes radiation reradiated by surface plasmons at a given radial position (as dependent on plasmon angle and amount of defocus, as discussed above), and also radiation reflected from the sample at a selected radial position (as deflected by the path altering element). The selected radial position was chosen to be substantially the same radius from the axis 99 of the beam as the radial position of plasmons appearing to come from the focus, so as to reduce the shot noise as much as possible. Light directly reflected from the sample along the optical axis 99 was blocked out in order to avoid saturating pixels at the centre of the detector, allowing greater sensitivity. This was achieved either by altering the profile of the incident beam using the SLM 84, or by masking a centre area of the CCD detector.

An image of the sample was built up by analysing the phase changes between the two components of received radiation as the amount of defocus was altered (i.e. as the stage 98 was moved forward or backward along the axis of the optical system). To build up an image of an area of the sample, the stage 98 was moved perpendicularly to the axis of the optical system in two dimensions, for example in a raster arrangement.

Figure 9:
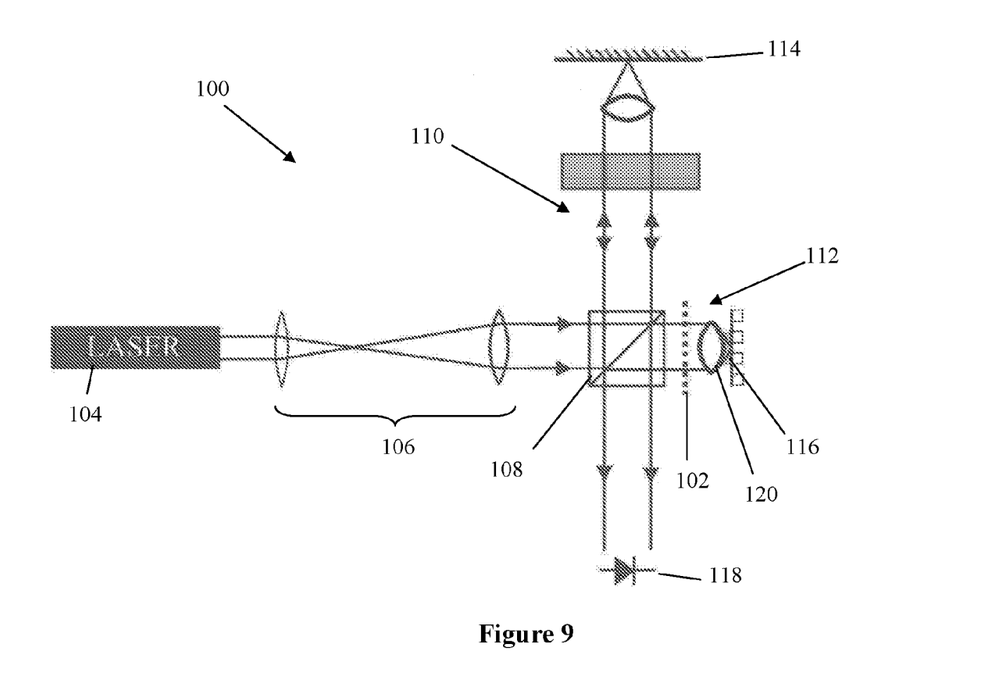
FIG. 9 is a simplified schematic diagram of an interferometric microscopy system.

FIG. 9 shows an alternative surface plasmon microscopy system 100, this time using an interferometric approach that does not require use of a confocal pinhole. The heterodyne interferometric system shown is similar to the system originally described in our previous patent WO01/92858, but with the additional inclusion of a path altering element 102, conjugate to the back focal plane, operable to cause the system to carry out the improved method described herein. In this case, as in the confocal system, blocking light from close to normal incidence is desirable.

The interferometric system 100 comprises an electromagnetic beam source 104, in particular a laser, in this case a 633 nm HeNe laser, and projection optics 106 which shape and direct the incident beam onto a beam splitter 108. The beam splitter is operable to split the incident beam of illumination into two components, a reference beam directed along reference arm 110 and a sample beam directed along sample arm 112 at 90 degrees to the reference arm. The two beam components are reflected respectively from a reference mirror 114 and the sample 116, and recombine at the beam splitter 108 where they are directed towards a detector 118.

The sample arm 112 includes an objective lens 120, in this case an oil immersion objective lens with a numerical aperture (NA) of 1.25, operable to focus radiation towards the sample. The numerical aperture used is dependent on the media being used, and should be selected as appropriate. For example, in aqueous media a higher NA, in the range 1.45 to 1.65, might be selected. As discussed above, if the sample 116 is placed off the focal plane of the lens (e.g. above the focal plane) a circle of radiation will be incident on the sample. As surface plasmons are excited only by radiation incident on the sample at a particular angle or range of angles, only an annulus of the circle of radiation will excite surface plasmons. In fact, where the incident radiation is linearly polarised, two part-annular arcs will excite surface plasmons, corresponding to the p-polarized portion of the beam. The remainder of the annulus, corresponding to the s-polarized portion of the beam, will not excite surface plasmons.

In the same way as with the confocal system described above, only radiation which appears to come from the focus of the objective lens will be returned to the detector along the sample arm and via the beam splitter. This radiation includes radiation reradiated by surface plasmons (along path P2), and radiation reflected from the sample which appears to originate at the focus (e.g. along path P1). However, the inclusion of the path altering element 102 means that reflected (i.e. s-polarised) radiation that would not otherwise reach the detector is deflected towards the detector (along path S1'). If required, the path altering element may also be operable to block out normally reflected light (i.e. light returning from the focus along the axis of the sample arm, following path P1).

As discussed above in connection with the confocal system, the more similar the radial location on the sample from which the reflected radiation originates is to the radial location on the sample from which the reradiated radiation originates, the smaller the effect of shot noise on the signal. Put another way, the closer the angle of reflection of the reflected component is to the angle of emission of the reradiated component, the smaller the noise component. The path altering element is therefore operable to deflect the radiation incident on it at a selected angle or angles through a predefined deflection angle d, such that the reflected radiation appears to appears to originate from the focus of the system. The deflection angle d will depend on the sample defocus and system magnification but will in general be a small fraction of a degree. Both the reflected and reradiated radiation components thus originate from an annular band on the sample surface having a defined radial depth.

The two components of radiation (reflected and reradiated) returning from the sample interfere. When the defocus of the system is varied, the phase difference between the radiation travelling along the two paths changes. Combing the two components of radiation with each other and a reference beam of radiation (from reference arm 110) results in an overall interference signal that magnitude of which (V(z)) will oscillate as the phase between the two paths changes. An image of the sample can be built up as discussed above, using the techniques described in WO01/92858.

Figure 10:
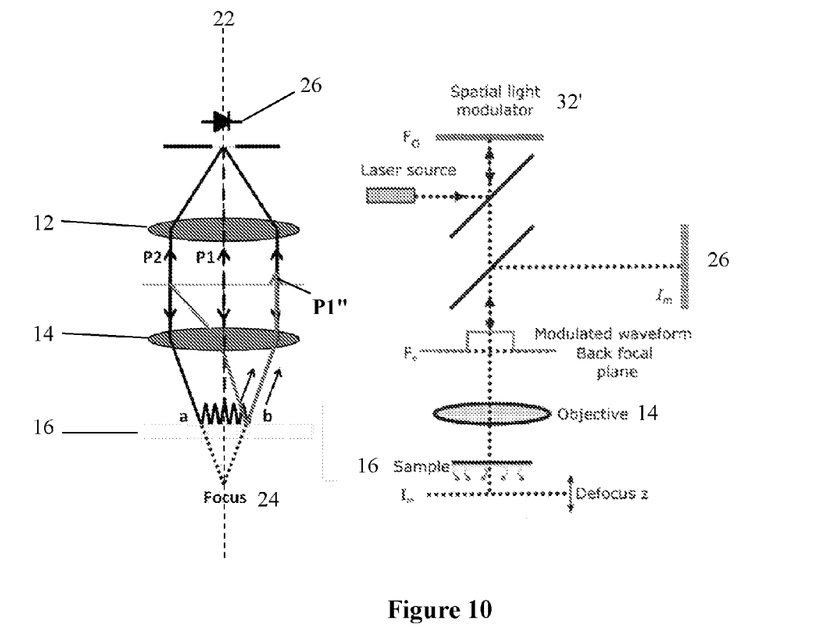
FIG. 10 is a simplified schematic diagram showing a confocal microscopy system having a path deflection element in the incident beam path, with a detail similar to FIG. 3 illustrating the light paths through the system.

A further example system in line with the principles discussed herein is shown in FIG. 10. This system is again a confocal system, and is similar to that of FIG. 3, hence like reference numerals have been used where appropriate.

As discussed above with reference to FIGS. 3 and 8, if an optical element 32, 96 is inserted into the return path of the electromagnetic beam that acts like a wedge (a linear phase gradient), the beam (or part of it) can be deflected parallel to the optical axis such that it will pass through the pinhole and be detected, when without deflection it would otherwise be blocked out by the pinhole. Alternatively, as in the system of FIG. 10, an optical element 32' can be placed in the path of the incident beam. Such an optical element is operable to deflect a portion of the incident radiation (in particular, in this example, an s-polarized portion) so that on reflection the deflected radiation appears to come from the focus 24. In particular, a portion of the incident beam can be deflected so that it follows the path P1". This path hits the sample at point 'b', which is at a similar radial position to the position from which surface plasmons following path P2 are emitted, and is reflected at a selected angle θ (similar to the angle at which surface plasmons are emitted).

Figure 11:
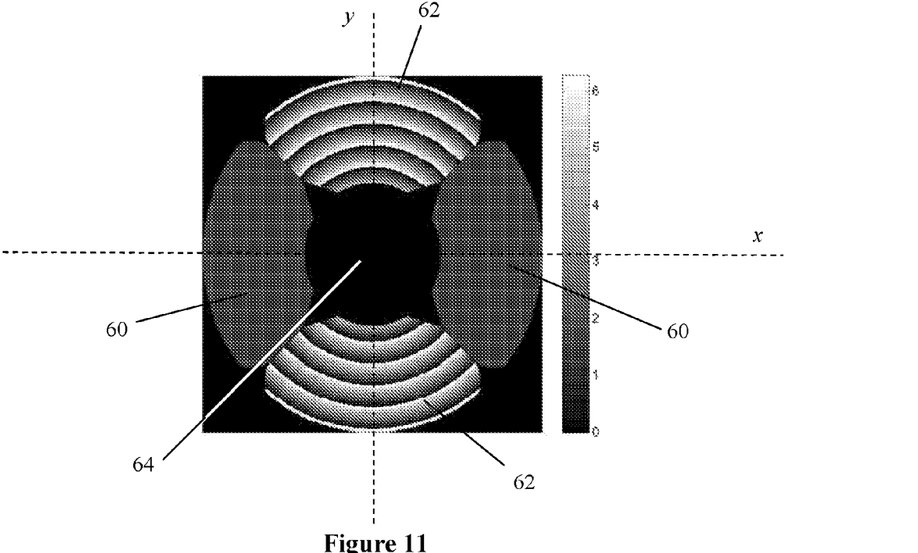
FIG. 11 shows the amplitude and phase pupil function provided by a spatial light modulator having a phase gradient in the two quadrants expecting to receive s-polarised radiation.

FIG. 11 shows a schematic of the pattern on the back focal plane used to effect the beam deflection in FIG. 10. This arrangement assumes the incident light is linearly polarized. In positions where the light is primarily p-polarized (marked 60) no linear phase gradient is applied as a portion of the reradiated SPs will appear to come from the focus. On the other hand, where light is predominantly s-polarized (marked 62), a linear phase gradient is applied. This gradient acts as a wedge prism, and light incident on it will interact with the wedge by bending and following path P1" of FIG. 10, thus returning to the pinhole (rather than following path S1 of FIG. 3 and being blocked out).

When the incident beam is linearly polarized it is apparent that only along orthogonal directions (x and y) is the incident light in a pure polarization state. For all other angles there is continuous variation of the relative proportions of the two polarization states. This does not, however, produce any fundamental issues. Any incident s-polarization that does not interact with the wedge will miss the pinhole. Similarly, any p-polarized light interacting with the wedge will be deviated beyond the normal and miss the pinhole on the other side.

As shown in FIG. 11, only light close to the angle for excitation of surface plasmons is allowed to pass through the back focal plane. Unwanted angles can be blocked out or otherwise masked, for example by setting pixels of a spatial light modifier (SLM) in the unrequired areas (for example, in a central area 64) in antiphase. The deflection element of the SLM (in this case the two wedge areas 62) is centred around the azimuthal angles corresponding to predominantly s-incident polarization. In the present example this corresponds to the two opposite quadrants of the SLM centred on the y axis. The exemplary deflection regions extend ±45 deg to either side of the y axis.

The wedge angle is controlled by the gradient of the phase shifts. For example, the wedge in FIG. 11 has an equivalent physical angle of 0.1 degree. It is also possible to phase shift one beam of the interferometer relative to the other by simply imposing a constant phase shift in the region corresponding to predominant p-polarization. In FIG. 11, for example, the p-polarization regions 60 are phase shifted with respect to the s-polarization regions 62 by 90 degrees.

In order to evaluate the system shown schematically in FIG. 10, a sample was fabricated having five different layer thicknesses (including zero) of indium tin oxide (ITO) deposited on a gold substrate used to support SPs. The layers were denoted R0, R1, R2, R3 and R4 respectively, with R0 being the thinnest (zero thickness) layer, and R4 being the thickest layer, and the thicknesses of the intermediate layers (R1, R2, R3) increasing incrementally in steps between R0 and R4.

Figure 12:
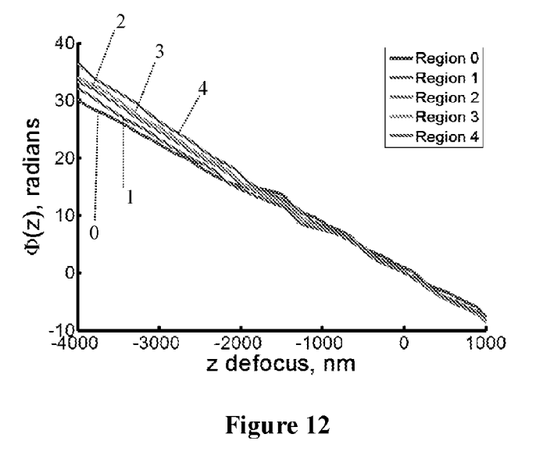
FIG. 12 shows the experimentally measured variation of phase difference $\phi(z)$ with defocus z for five difference thicknesses of material with a normally incident reference beam.

In order to obtain an independent measure of the thickness of the layers these were measured from the top surface using a spectroscopic ellipsometer (alpha-SE J. A. Woollam (Inc)). We then measured the same sample with different configurations of the SP microscope. The first set of SP measurements used the approach described above with reference to FIG. 1, where a normally incident reference beam was used to interfere with the SP waves. Four 90 deg. phase steps were imposed on the reference beam so that a phase stepping algorithm could be used to extract the phase difference between the normally incident and the plasmonic contributions. This phase difference, φ, can be plotted against the defocus, z, as shown in FIG. 12.

The mean gradient of this phase variation can be related to the angle of plasmon excitation thus:

$$\frac{d\phi(z)}{dz} = \frac{4\pi}{\lambda}(\cos\theta_r - \cos\theta_p) \qquad [2]$$

where $\theta_r$ is the mean incident angle of the reference beam (which is in the case of the system of FIG. 1 is zero) and $\theta_p$ is the mean angle at which SPs are excited.

FIG. 12 shows the measured values of φ(z) and from the gradients measured in the defocus region between −4000 and −2000 nm we can obtain a value of $\theta_p$ for each sample region by estimating the mean gradient of the curve and fitting to equation. Note that negative values of defocus correspond to moving the sample closer to the objective relative to the focal point. If we assume the same refractive index as used to fit the ellipsometric data (n=1.8583) we can recover a film thickness from the SP measurements from the Fresnel equations (available in Hecht E. Optics. Addison-Wesley Longman, Incorporated, 2002) to calculate $\theta_p$ for different layer thicknesses. It should be noted that unlike the ellipsometric measurements the SP measurements are obtained from below the sample surface; that is through the gold film. The thickness values obtained are tabulated in the second and third columns of Table 1.

TABLE 1

Thickness values obtained by ellipsometric, phase stepping and artificial plasmon methods

| Region | Ellipsometry | Phase Stepping | Artificial plasmon |
|---|---|---|---|
| R0 | 0.00 nm | 0.00 nm | 0.08 nm |
| R1 | 3.31 nm | 2.97 nm | 2.83 nm |
| R2 | 6.32 nm | 5.31 nm | 5.23 nm |
| R3 | 8.02 nm | 7.75 nm | 7.67 nm |
| R4 | 10.00 nm | 10.53 nm | 10.50 nm |

The agreement in the obtained thickness values between the ellipsometry measurements and the phase stepping measurements are good. Some of the discrepancy between the measurements arises from fact that the exact measurement position on the sample may differ.

Figure 13:
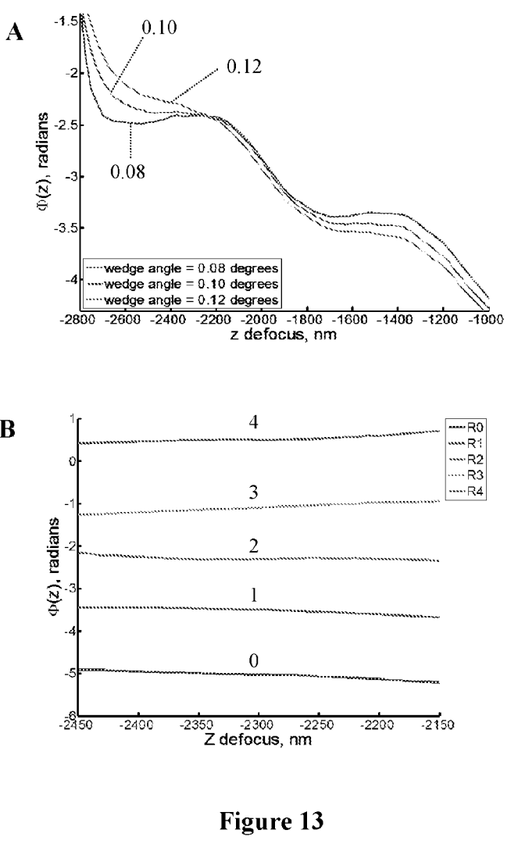
FIG. 13 shows the experimentally measured variation of phase difference $\phi(z)$ with defocus z for a system as described herein for (A) three difference path deflection angles, and (B) five difference thicknesses of material. The labels on the curves refer to the sample region.

We then used the 'artificial' plasmon approach described herein with reference to FIGS. 3, 8, 9 and 10 to perform similar measurements on the same five layered sample. FIG. 13A shows the phase variation on sample region R2 for different wedge angles or phase gradients imposed in the back focal plane. The wedge was formed by a staircase pattern imposed on the SLM, similar to that shown in FIG. 11, and the wedge angle was controlled by changing the gradient of the staircase. We see that from a defocus of −1000 nm the gradient is much less than that obtained with the normally incident reference beam. We note, however, that there are two regions where the phase is stationary with defocus. We can also see that careful tuning of the wedge angle gives a flat region for a particular sample region. For regions R3 and R4 similar flat regions are obtained for larger wedge angles and for R0 and R1 for smaller wedge angles. These regions of flat phase variation do not extend over large regions of defocus; nevertheless, this modest range of flat response was adequate to demonstrate the superior noise immunity of the present system.

The longer the range of defocus used to calculate the wave vector of the surface plasmon the more accurate the measurement. On the other hand, we have found that reducing the maximum defocus improves the lateral resolution. Using the 'artificial plasmon' method described herein to measure the local gradient over a narrow range of defocus corresponding to the flat region from −2400 nm to −2100 nm, by phase stepping the region with predominant p-polarization we obtained curves for the variation of $\phi(z)$ shown in FIG. 13B for the five regions of the sample. We then used the measured gradients in equation 2 (with $\theta_r$ equal to $\theta_p$ for the R2 region). These values are shown in the final column Table 1, and show excellent agreement with results involving a normally incident reference beam.

The results above were all obtained with our optical table pumped up in order to suppress noise. To test the noise performance the legs of the table were deflated and the large bass speaker was placed on the optical table to induce large amounts of microphonic noise. The measurements were then repeated for the normal incidence interferometer and the 'artificial' plasmon interferometer.

To get an estimate of the noise in thickness measurements we measured the noise in the $\phi(z)$ curves from the deviation of the measured phase shifts from their best linear fitted results. We then used this noise variance to generate a new set of data with the same underlying statistics; this was then used to get another estimate of $\phi(z)$ from which a new estimate of thickness was obtained. This process was repeated $10^6$ times to get the noise statistics presented in FIG. 14.

Figure 14:
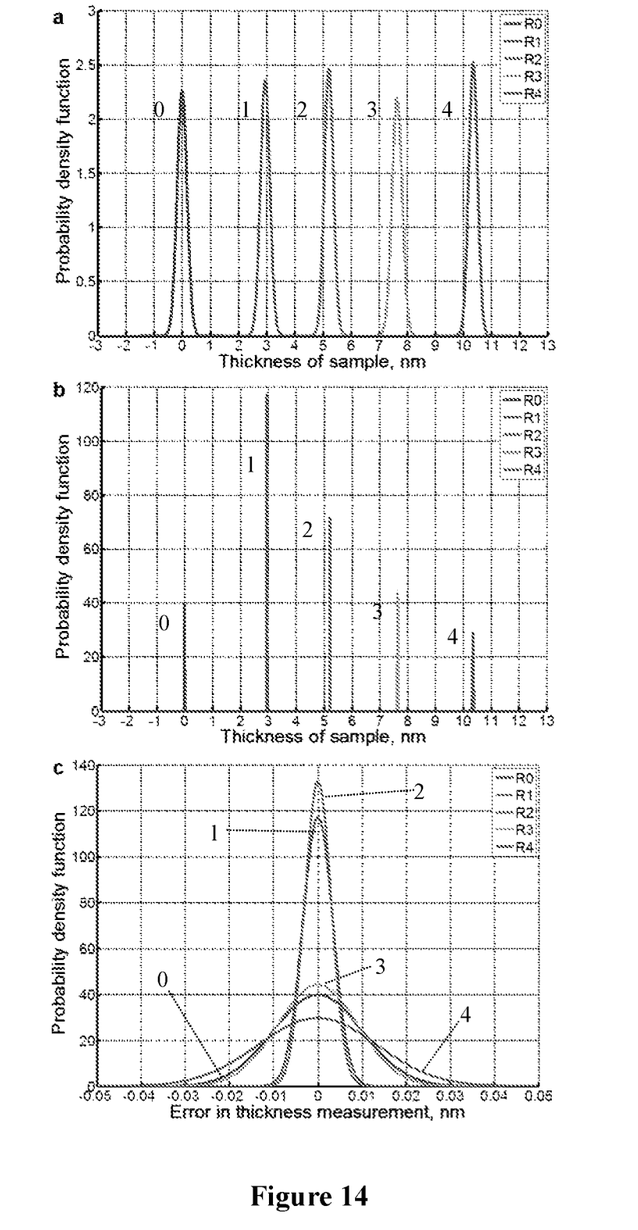
FIG. 14 shows (a) probability distributions (error) obtained from experimental measurements as a function of sample thickness in the measurements of FIG. 12 using a normally incident reference beam, (b) probability distributions (error) as a function of sample thickness in the measurements of FIG. 13 with a reference beam incident at an angle close to the surface plasmon incident angle. Note the major reduction in noise uncertainty with the oblique reference beam (see table 2), and (c) zoomed in plot of probability distributions similar to (b) under noisy conditions. The labels on the curves refer to the sample region.

FIGS. 14a and 14b show Gaussian curves obtained from the measured noise variance of the two methods. We see as expected a dramatic improvement in noise performance in the 'artificial' plasmon system, which are tabulated in Table 2. If we compare the results for R2 where the wedge angle is best matched to the expected value of $\theta_p$, we see that the noise standard deviation is 54 times better for the 1000 nm scan and 35 times less compared to the 2000 nm scan. Once the starting point for a typical biomedical measurement have been established the changes of $\theta_p$ vary by smaller amounts than in the current experiments, so the noise immunity provided by a single wedge angle is likely to apply to the whole measurement. If this were not the case the use of the electronically programmable SLM means it is easy to vary the wedge angle interactively as the measurement proceeds. The system as presented thus has the potential for optimal performance in terms of sensitivity, spatial resolution and dynamic range. These three key characteristics have not hitherto been achieved in a single system.

TABLE 2

Standard deviation $\sqrt{\sigma^2}$ of thicknesses of the sample

Standard deviation $\sqrt{\sigma^2}$ of thicknesses in nm

| Sample region | Phase stepping Z defocus distance = 2000 nm | Phase stepping Z defocus distance = 1000 nm | Artificial plasmon Z defocus distance = 300 nm |
|---|---|---|---|
| R0 | 0.1053 | 0.1761 | 0.0098 |
| R1 | 0.1084 | 0.1688 | 0.0032 |
| R2 | 0.1053 | 0.1621 | 0.0030 |
| R3 | 0.1145 | 0.1823 | 0.0089 |
| R4 | 0.1022 | 0.1582 | 0.0132 |

In the examples described above, we used a linear wedge in all the measurements which gives a measurement range with good phase cancellation of around 300 nm. However, we have found that the flat region in the phase variation discussed above can be extended by using a 'curved' wedge that deviates from the perfect linear case. An example of such a curved wedge is shown in FIG. 15.

Figure 15:
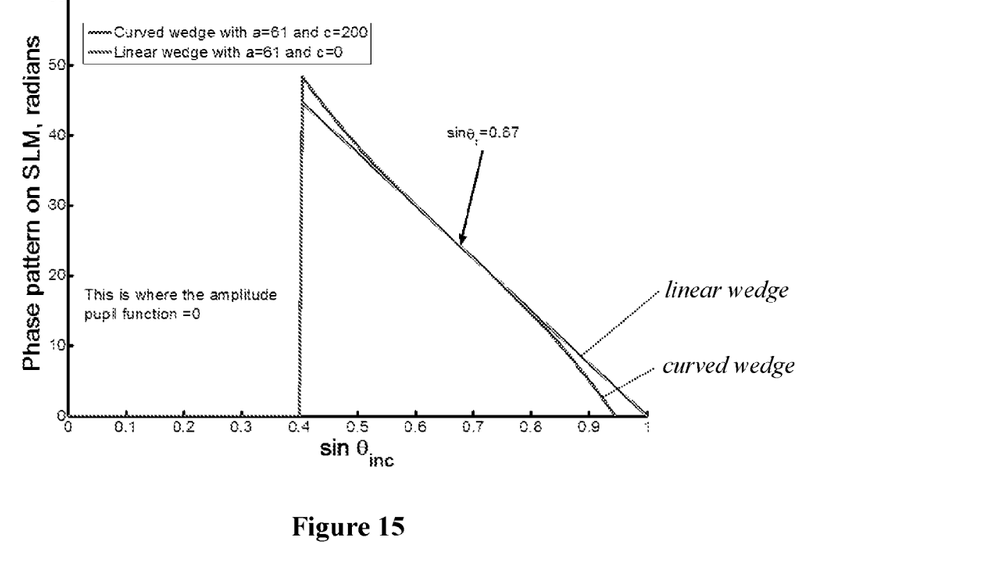
FIG. 15 contrasts a linear wedge with a curved wedge showing phase variation vs. sine of the incident angle determined by radial position in the back focal plane; where the curved-wedge can be generated using third order polynomial equation with a=61, b=200 and sin $\theta_2$=0.67.
Figure 16:
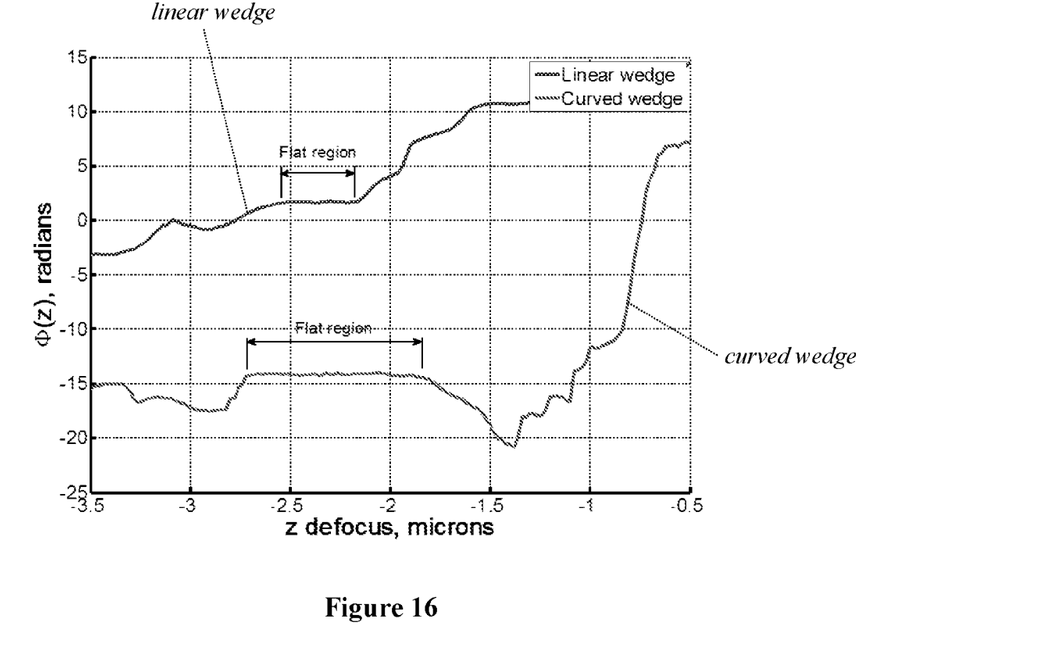
FIG. 16 shows the phase difference $\phi(z)$ curves corresponding to the wedges in FIG. 15 where the third order beam extends the region where the phase is flat. The flat region is the region where the effect of microphonic noise cancels.

The wedge in FIG. 15 was constructed by adding a simple cubic term into the phase gradient to introduce some curvature, as shown in eq. 3.

$$\phi(\sin\theta) = a(\sin\theta - \sin\theta_r) + c(\sin\theta - \sin\theta_r)^3 \quad [3]$$

where a is the gradient of the wedge and the c is the parameter that is varied to get optimum region with flat phase response. The comparison between the linear wedge and the example curved wedge of FIG. 15 is shown in FIG. 16, in which we can see that the curved wedge can extend the flat region to around 1 micron. These results were obtained using a 1.49 NA oil immersion objective (Nikon) and laser source (690 nm laser).

It will be appreciated that the curved wedge shown in FIG. 15 is not the only possibility. Wedges having an alternative curvature are possible. Such wedges may include a gradient having a cubic component, but need not necessarily.

The methods and systems described herein can be used to obtain surface plasmon microscopy images having improved stability over prior techniques. We have determined that interfering radiation emitted by surface plasmons with radiation reflected from the sample which is not aligned with the axis of the beam illuminating the sample results in a reduction in microphonic noise in the resulting interference signal. We have further determined that using a path deflection element having a curved gradient can improve the versatility of the system by extending the region of defocus at which the phase variation remains stationary with defocus.

The invention claimed is:

1. A surface plasmon microscopy method comprising:
   irradiating a sample with a beam of electromagnetic radiation, wherein at least some of the radiation is incident on the sample at an angle or angles which results in the excitation of surface plasmons in the sample, and wherein the beam of radiation comprises a longitudinal axis passing through a focus of the beam;
   receiving at a detector radiation reradiated from the sample by one or more surface plasmons;
   receiving at a detector radiation reflected from a location on the sample which does not lie on the longitudinal axis passing through the focus; and interfering the received reradiated radiation with the received reflected radiation.

2. The method of claim 1, wherein the reflected radiation is reflected at an angle θ which is substantially the same as the angle or angles at which surface plasmons are generated.

3. The method of claim 1, wherein the reflected radiation is reflected from a position on the sample surface which has substantially the same radius from the longitudinal axis of the beam as the position from which the received radiation reradiated by the one or more surface plasmons was emitted.

4. The method of claim 1, wherein the method is substantially common path.

5. The method according to claim 1, wherein the beam of electromagnetic radiation is linearly polarized.

6. The method of claim 5, wherein the received reradiated radiation is p-polarized, and wherein the received reflected radiation is s-polarized.

7. The method of claim 1, wherein receiving the reflected radiation at the detector includes deflecting the path of the reflected radiation through a deflection angle d and/or deflecting the path of the incident radiation through a deflection angle d.

8. The method of claim 1, further comprising masking the electromagnetic beam such that radiation on the longitudinal axis of the system is not detected.

9. The method of claim 8, wherein the masking comprises (i) masking an area of a detector; and/or (ii) masking an area of the beam; and/or (iii) programming a detector to disregard radiation detected in a pre-programmed area.

10. The method of claim 1, wherein the method is confocal.

11. The method of claim 1, wherein the method is interferometric.

12. A surface plasmon microscopy system comprising a radiation source and a detector, the system adapted to:
   irradiate, using the radiation source, a sample with a beam of electromagnetic radiation, wherein at least some of the radiation is incident on the sample at an angle or angles which results in the excitation of surface plasmons in the sample, and wherein the beam of radiation comprises a longitudinal axis passing through a focus of the beam;
   receive, at the detector, radiation reradiated from the sample by one or more surface plasmons;
   receive, at the detector, radiation reflected from a location on the sample which does not lie on the longitudinal axis passing through the focus; and
   interfer the received reradiated radiation with the received reflected radiation.

13. The system of claim 12, wherein the reflected radiation is reflected at an angle θ which is substantially the same as the angle or angles at which surface plasmons are generated.

14. The system of claim 12, wherein the reflected radiation is reflected from a position on the sample surface which has substantially the same radius from the longitudinal axis of the beam as the position from which the received radiation reradiated by the one or more surface plasmons was emitted.

15. The system according to claim 12, wherein the beam of electromagnetic radiation is linearly polarized, wherein the received reradiated radiation is p-polarized, and wherein the received reflected radiation is s-polarized.

16. The system of claim 12, wherein the system includes a path altering element operable to deflect the path of the reflected radiation through a deflection angle d and/or a path altering element operable to deflect the path of a portion of the incident radiation through a deflection angle d.

17. The system of claim 16, wherein the path altering element comprises:
   (i) a substantially linear gradient; or
   (ii) a curved gradient.

18. A computer program encoded on a non-transitory computer readable medium, the computer program operable, when run, to cause a surface plasmon microscopy system comprising a radiation source and a detector to:
   irradiate, using the radiation source, a sample with a beam of electromagnetic radiation, wherein at least some of the radiation is incident on the sample at an angle or angles which results in the excitation of surface plasmons in the sample, and wherein the beam of radiation comprises a longitudinal axis passing through a focus of the beam;
   receive, at the detector, radiation reradiated from the sample by one or more surface plasmons;
   receive, at the detector, radiation reflected from a location on the sample which does not lie on the longitudinal axis passing through the focus; and
   interfer the received reradiated radiation with the received reflected radiation.

* * * * *